US008436157B2

(12) United States Patent
Wiley, Jr. et al.

(10) Patent No.: US 8,436,157 B2
(45) Date of Patent: *May 7, 2013

(54) METHOD FOR THE PRODUCTION OF SUCRALOSE

(75) Inventors: James Edwin Wiley, Jr., Daphne, AL (US); Duane A. Leinhos, Satsuma, AL (US); David A. Dentel, Singapore (SG); John Kerr, South Croydon (GB)

(73) Assignee: Tate & Lyle Technology Limited, London (GB)

( * ) Notice: Subject to any disclaimer, the term of this patent is extended or adjusted under 35 U.S.C. 154(b) by 564 days.

This patent is subject to a terminal disclaimer.

(21) Appl. No.: 12/409,951

(22) Filed: Mar. 24, 2009

(65) Prior Publication Data

US 2009/0247737 A1    Oct. 1, 2009

Related U.S. Application Data

(60) Provisional application No. 61/039,616, filed on Mar. 26, 2008.

(51) Int. Cl.
*C07H 1/00* (2006.01)
(52) U.S. Cl.
USPC ........................................................ 536/18.5
(58) Field of Classification Search .................. 536/18.5
See application file for complete search history.

(56) References Cited

U.S. PATENT DOCUMENTS

| | | | |
|---|---|---|---|
| 4,362,869 A | 12/1982 | Jenner et al. | |
| 4,380,476 A | 4/1983 | Mufti et al. | |
| 4,405,654 A | 9/1983 | Lee | |
| 4,783,526 A | 11/1988 | O'Brien et al. | |
| 4,826,962 A | 5/1989 | Rathbone et al. | |
| 4,889,928 A | 12/1989 | Simpson | |
| 4,950,746 A | 8/1990 | Navia | |
| 4,980,463 A * | 12/1990 | Walkup et al. | 536/124 |
| 5,023,329 A | 6/1991 | Neiditch et al. | |
| 5,034,551 A | 7/1991 | Vernon et al. | |
| 5,089,608 A | 2/1992 | Walkup et al. | |
| 5,128,248 A | 7/1992 | Dordick et al. | |
| 5,141,860 A | 8/1992 | Bornemann et al. | |
| 5,270,071 A | 12/1993 | Sharp et al. | |
| 5,272,137 A | 12/1993 | Blase et al. | |
| 5,298,611 A | 3/1994 | Navia et al. | |
| 5,354,902 A | 10/1994 | Merciadez et al. | |
| 5,374,659 A | 12/1994 | Gowan | |
| 5,384,311 A | 1/1995 | Antenucci et al. | |
| 5,397,588 A | 3/1995 | Antenucci et al. | |
| 5,409,907 A | 4/1995 | Blase et al. | |
| 5,426,220 A | 6/1995 | Baniel et al. | |
| 5,440,026 A | 8/1995 | Khan et al. | |
| 5,470,969 A | 11/1995 | Sankey et al. | |
| 5,498,709 A | 3/1996 | Navia et al. | |
| 5,530,106 A | 6/1996 | Navia et al. | |
| 5,593,696 A | 1/1997 | McNally et al. | |
| 5,621,005 A | 4/1997 | Gowan | |
| 5,658,919 A | 8/1997 | Ratnaraj et al. | |
| 5,674,522 A | 10/1997 | Shah et al. | |
| 5,817,340 A | 10/1998 | Roche et al. | |
| 5,876,759 A | 3/1999 | Gowan | |
| 5,977,349 A * | 11/1999 | Catani et al. | 536/124 |
| 6,080,481 A | 6/2000 | Ochs et al. | |
| 6,090,401 A | 7/2000 | Gowan et al. | |
| 6,176,935 B1 * | 1/2001 | Brahmbhatt | 127/52 |
| 6,211,246 B1 | 4/2001 | Gelotte et al. | |
| 6,258,381 B1 | 7/2001 | Luber et al. | |
| 6,265,012 B1 | 7/2001 | Shamil | |
| 6,277,409 B1 | 8/2001 | Luber et al. | |
| 6,646,121 B2 | 11/2003 | El Kabbani et al. | |
| 6,723,877 B1 * | 4/2004 | Maliszewskyj et al. | 564/215 |
| 6,809,198 B2 | 10/2004 | El Kabbani et al. | |
| 6,890,581 B2 | 5/2005 | Vernon et al. | |
| 6,939,962 B2 | 9/2005 | Clark et al. | |
| 6,943,248 B2 | 9/2005 | Catani et al. | |

(Continued)

FOREIGN PATENT DOCUMENTS

DE    102 60 085    7/2004
EP    0043649    1/1982

(Continued)

OTHER PUBLICATIONS

DeSilva, Frank, Water Quality Products. 2006, 1194), pp. 1-3.*
Boers, Rutger; Combined Search and Examination Report; Jul. 18, 2008; 6 pp; South Wales.
Bonomelli, Federico and Bardili, Burkhart; International Search Report; Aug. 24, 2009; 11 pp; European Patent Office, Rijswijk, The Netherlands.
Ault, A., Techniques and Experiments for Organic Chemistry, 1987, pp. 43-45, 54.
Chen et al., Han-Ping, "A Down-Exhaust Cyclone Separator," Ind. Eng. Chem. Res., 1999, 38, pp. 1605-1610.

(Continued)

*Primary Examiner* — Shaojia Anna Jiang
*Assistant Examiner* — Ganapathy Krishnan
(74) *Attorney, Agent, or Firm* — RatnerPrestia

(57) ABSTRACT

The present invention provides a method for producing sucralose from a feed stream including a sucrose-6-acylate in a reaction vehicle. The method includes:
(i) reacting the sucrose-6-acylate with a chlorinating agent in order to chlorinate the 4, 1' and 6' positions of the sucrose-6-acylate;
(ii) quenching the product stream of (i) with an aqueous solution of a base to provide a sucralose-6-acylate and the chloride salt of said base, wherein the concentration of the aqueous solution of the base is sufficiently high such that at least a portion of the chloride salt of the base is formed as a precipitate;
(iii) either:
deacylating the sucralose-6-acylate by treating the product stream of (ii) with a base and thereafter removing precipitated salt to provide a product stream including sucralose;
or:
removing precipitated salt from the product stream of (ii) and thereafter deacylating the sucralose-6-acylate by treating with a base to provide a product stream including sucralose; and
(iv) isolating sucralose from the product stream of (iii).

41 Claims, No Drawings

U.S. PATENT DOCUMENTS

| | | |
|---|---|---|
| 6,998,144 B2 | 2/2006 | Merkel et al. |
| 6,998,480 B2 | 2/2006 | Catani et al. |
| 7,049,435 B2 | 5/2006 | Catani et al. |
| 2002/0157937 A1 | 10/2002 | Cockrem et al. |
| 2004/0030124 A1 | 2/2004 | Catani et al. |
| 2006/0149084 A1 | 7/2006 | Domschke et al. |
| 2006/0188629 A1 | 8/2006 | Liesen et al. |
| 2006/0205936 A1 | 9/2006 | Jia et al. |
| 2006/0276639 A1 | 12/2006 | Fry |
| 2007/0015916 A1 | 1/2007 | El Kabbani et al. |
| 2007/0100139 A1 | 5/2007 | Fry |
| 2007/0160732 A1 | 7/2007 | Deshpande et al. |
| 2007/0227897 A1 | 10/2007 | Li et al. |
| 2007/0270583 A1 | 11/2007 | Ratnam et al. |
| 2008/0227971 A1 | 9/2008 | Leinhos et al. |

FOREIGN PATENT DOCUMENTS

| | | |
|---|---|---|
| EP | 0409549 | 1/1991 |
| EP | 0708110 | 4/1996 |
| EP | 0708110 A2 * | 4/1996 |
| GB | 1426018 | 2/1976 |
| WO | WO 00/14052 | 3/2000 |
| WO | WO 02/074403 | 9/2002 |
| WO | WO 03/076453 | 9/2003 |
| WO | WO 03/076454 | 9/2003 |
| WO | WO 2005/090374 | 9/2005 |
| WO | WO 2005/090374 A1 * | 9/2005 |
| WO | WO 2005/090376 | 9/2005 |
| WO | WO 2005/090376 A1 * | 9/2005 |
| WO | WO 2006/061855 | 6/2006 |
| WO | WO 2006/130169 | 12/2006 |
| WO | WO 2007/017899 | 2/2007 |
| WO | WO 2007/023505 | 3/2007 |
| WO | WO 2007/023505 A2 * | 3/2007 |
| WO | WO 2007/052304 | 5/2007 |
| WO | WO 2008/004246 | 1/2008 |
| WO | WO 2008/091539 | 7/2008 |

OTHER PUBLICATIONS

Grant, et al., Roger, Chemical Dictionary, 1987, p. 122.
Qin, et al., Yingjie, "Pervaporation Membranes That Are Highly Selective for Acetic Acid Over Water," *Ind. Eng. Chem. Res.*, 42, (2003), pp. 582-595.
Schierbaum, et al., Burkhard, "Isolation of Carboxylic Acids from Aqueous Solutions by Extraction with Dialkylcarboxylic Amides/Trialkylamines," Chem. Eng. Technol. 22 (1999) 1, pp. 37-41.
Smith et al., Jim, Food Additives Databook, 2003, p. 988.
The Free Dictionary, McGraw-Hill, 2003, pp. 1-2.
The Merck Index, 1996, p. 549.

\* cited by examiner

METHOD FOR THE PRODUCTION OF SUCRALOSE

CROSS REFERENCE TO RELATED APPLICATIONS

This application claims priority benefit of U.S. Provisional Appln. No. 61/039,616, filed Mar. 26, 2008, the entirety of which is incorporated herein by reference.

The present invention relates to an improved method for producing sucralose. In particular, the present invention relates to a method for producing sucralose from a feed stream comprising a sucrose-6-acylate in a reaction vehicle. The present invention also provides a method for producing sucralose-6-acylate, which is an intermediate in a production process for sucralose.

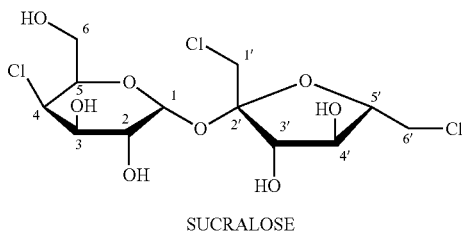

SUCRALOSE

Methods for producing sucralose intermediates and sucralose from a feed stream comprising a sucrose-6-acylate in a reaction vehicle are known. For example, EP 0409549 discloses a process for the chlorination of a sucrose-6-acylate in a tertiary amide reaction vehicle to produce a sucralose-6-acylate, such as sucralose-6-acetate. A large excess of an acid chloride, such as phosgene, is used as the chlorination agent in this process. Following the chlorination reaction, the excess chlorinating agent is quenched using a suitable base, thereby forming the chloride salt of the base. The resulting product stream thus comprises a sucralose-6-acylate, the tertiary amide reaction vehicle, water, and salts.

A known method for obtaining sucralose from a product stream comprising a sucralose-6-acylate, a tertiary amide reaction vehicle, water, and salts, without isolation of the sucralose-6-acylate intermediate, is disclosed in EP 0708110. The process comprises deacylation of the sucralose-6-acylate before or after removal of the tertiary amide reaction vehicle, and then isolation of the sucralose. The removal of the tertiary amide (which is usually DMF) is carried out by steam stripping.

According to EP 0708110, it is preferred to perform the deacylation after the removal of the reaction vehicle, because otherwise, during the deacylation step, base-catalysed decomposition of the reaction vehicle, in this case a tertiary amide, occurs. This hinders the subsequent isolation of the sucralose, and also means that the tertiary amide cannot be efficiently recovered and recycled. Thus, the tertiary amide reaction vehicle is removed from an aqueous solution of sucralose-6-acylate, and deacylation of the sucralose-6-acylate is carried out thereafter.

The preferred process according to EP 0708110 requires that a large amount of water is present in the process stream during the removal of the tertiary amide. This is necessary to ensure that the high concentration of salts is maintained in solution, thereby minimising the amount of solids that the process stream has to accommodate. The large amount of water also ensures that the sucralose-6-acylate, which is soluble in the tertiary amide reaction vehicle but less soluble in water, is maintained in solution as the tertiary amide reaction vehicle is removed.

The large amount of water that is present in the process stream of EP 0708110 during the removal of the tertiary amide reaction vehicle has the effect that the removal of the tertiary amide reaction vehicle, for example by steam stripping, is very energy intensive. It would be advantageous if the amount of water present during this operation could be reduced, in order to increase the energy efficiency of the process.

The disadvantages of the known steam stripping process for removal of the reaction vehicle are discussed in WO 2005/090376 and WO 2005/090374. Here it is proposed to remove all liquids from the chlorination feed to provide a solid residue, and to then obtain sucralose from the solid residue. According to this prior art, the removal of the liquids preferably takes place using an agitated thin film dryer.

A further disadvantage associated with the process of EP 0708110 is that the salts are maintained in the process stream and are only removed during the final isolation of sucralose. The presence of high concentrations of salts in the process stream limits opportunities to employ salt-sensitive purification techniques on the process stream. Furthermore, removal of salts only during the final isolation of sucralose results in a waste stream that contains a high concentration of salts, as well as other impurities. The high level of salts in the waste stream makes the treatment of the waste stream difficult. It would be advantageous if the concentration of salts both in the process stream and also in the waste stream obtained during the final isolation of sucralose could be minimised.

With the above in mind, the present inventors have devised an improved process for the production of sucralose.

SUMMARY OF THE INVENTION

Thus, in a first aspect, the present invention provides a method for producing sucralose from a feed stream comprising a sucrose-6-acylate in a reaction vehicle, wherein said method comprises:

(i) reacting the sucrose-6-acylate with a chlorinating agent in order to chlorinate the 4, 1' and 6' positions of the sucrose-6-acylate;

(ii) quenching the product stream of (i) with an aqueous solution of a base to provide a sucralose-6-acylate and the chloride salt of said base, wherein the concentration of the aqueous solution of the base is sufficiently high such that at least a portion of the chloride salt of the base is formed as a precipitate; and (iii) either:

deacylating the sucralose-6-acylate by treating the product stream of (ii) with a base and thereafter removing precipitated salt to provide a product stream comprising sucralose;

or:

removing precipitated salt from the product stream of (ii) and thereafter deacylating the sucralose-6-acylate by treating with a base to provide a product stream comprising sucralose.

In a preferred embodiment, the first aspect of the present invention further comprises:

(iv) isolating sucralose from the product stream of (iii).

In a second aspect, the present invention provides a method for producing a sucralose-6-acylate product stream from a feed stream comprising a sucrose-6-acylate in a reaction vehicle, wherein said method comprises:

(i) reacting the sucrose-6-acylate with a chlorinating agent in order to chlorinate the 4, 1' and 6' positions of the sucrose-6-acylate;

(ii) quenching the product stream of (i) with an aqueous solution of a base to provide the sucralose-6-acylate and the chloride salt of said base, wherein the concentration of the aqueous solution of the base is sufficiently high such that at least a portion of the chloride salt of the base is formed as a precipitate; and (iii) removing precipitated salt from the product stream of (ii) to provide a sucralose-6-acylate product stream.

In a preferred embodiment, the second aspect of the present invention further comprises the conversion of sucralose-6-acylate to sucralose to provide a sucralose product stream. Sucralose can then be isolated from the sucralose product stream.

Various other advantageous embodiments and further developments of the processes according to the first and second aspects of the present invention are set out in the dependent claims.

DETAILED DESCRIPTION OF THE INVENTION

Thus, according to the first aspect of the present invention, a product stream resulting from the chlorination of sucrose-6-acylate is quenched with a base of sufficiently high concentration that at least a portion of the chloride salt of the base is formed as a precipitate. The precipitated salt may then be removed from the process stream either before or after the deacylation reaction, and sucralose can then be isolated from the resulting desalinated product stream.

The removal of salts from the process stream of the present invention prior to the isolation of sucralose provides a number of advantages. One advantage is that the waste stream produced during the isolation of sucralose has a much lower salt content than the waste streams of prior art processes, which allows the waste stream to be treated more easily.

A further advantage of the process according to the present invention is that the volume of water that is present in the process stream is significantly reduced, which allows significant energy savings to be made downstream. This saving is especially notable if the reaction vehicle is subsequently removed by steam stripping, and could enable the energy costs for steam stripping to be reduced by as much as 75 to 80%. The reduction in the water content of the process stream also allows the use of smaller reaction vessels, with corresponding cost savings.

The reduction in water content achieved in the process of the present invention was not possible in prior art processes, since sufficient water needed to be present to ensure that the high concentration of salts remained in solution, and to ensure that the sucralose-6-acylate remained in solution during and after the removal of the reaction vehicle.

According to the present invention, however, at least a portion of the salts is removed from the process stream, so that the problem of maintaining them in solution is reduced or eliminated. Furthermore, in contrast to the preferred process of EP 0708110 where the reaction vehicle is removed prior to deacylation, and thus from a sucralose-6-acylate process stream, the present invention provides that deacylation of sucralose-6-acylate takes place in the presence of reaction vehicle, to provide a process stream containing sucralose. Subsequent removal of reaction vehicle therefore takes place from a sucralose product stream, rather than from a sucralose-6-acylate product stream. By virtue of having a further free hydroxyl group in place of an ester group, sucralose is more soluble in water than sucralose-6-acylate. This higher solubility means that less water needs to be present in order to maintain the desired species in solution.

In the light of EP 0708110, it is surprising that deacylation can be carried out in an effective manner in the presence of the reaction vehicle. According to EP 0708110, it was preferred to remove the reaction vehicle prior to carrying out deacylation. This order was preferred in order to avoid decomposition of the reaction vehicle under the deacylation conditions, which reduced the yield of reaction vehicle available to be recovered and subsequently recycled. It also introduced decomposition products as impurities in the product stream.

Contrary to the teaching of EP 0708110, it has now been found that, provided that the reaction conditions are controlled carefully, deacylation can be achieved with minimal decomposition of the reaction vehicle, usually a tertiary amide. Accordingly, it is possible to carry out deacylation prior to the removal of the reaction vehicle, and to then recover the reaction vehicle from a process stream containing sucralose.

Besides allowing for a reduction in the amount of water that needs to be present in the process stream in order to maintain the desired species in solution, the ability to perform deacylation in the presence of the reaction vehicle has a number of further advantages for the process, especially where the reaction vehicle is subsequently removed by steam stripping. These advantages include the fact that the undesired solids that are generated by the steam stripping process are less inclined to trap significant quantities of the desired product. Accordingly, the final yield of sucralose is increased.

As used herein, the term "reaction vehicle" means the diluent or solvent in which the chlorination reaction is performed. The term is meant to indicate that the vehicle may not fully dissolve all the components of the reaction and product mixture.

The sucrose-6-acylate can be any acylate that serves to protect the 6-hydroxy group during the chlorination reaction. It is preferably an aliphatic or carbocyclic aromatic acylate, more preferably a benzoate or acetate, and most preferably an acetate.

The chlorination reaction in the method of the present invention can be carried out by a number of methods, such as those disclosed in EP 0043649, EP 0409549, US 2006/0205936, and US 2007/0100139.

A number of chlorinating agents may be used in the present invention in order to chlorinate the 4, 1' and 6' positions of the sucrose-6-acylate. Suitable examples include those selected from the group consisting of phosgene, Arnold's reagent (also known as (chloromethylene)dimethyliminium chloride or as (chloromethylene)dimethylammonium chloride), phosphorous oxychloride, phosphorous pentachloride, thionyl chloride, oxalyl chloride, methanesulfonyl chloride, sulfuryl chloride, diphosgene (trichloromethyl chloroformate) and triphosgene (bis(trichloromethyl)carbonate). Other suitable chlorinating agents known to the skilled person may also be used. Preferably, the chlorinating agent is phosgene or Arnold's reagent.

Depending on the chlorinating agent employed, a number of types of reaction vehicles may be used, and any reaction vehicle can be used that is stable under the chlorination conditions and that dissolves the starting materials, reagents, and products at least to some extent, for example aromatic hydrocarbons such as xylene or toluene; chlorinated hydrocarbons such as trichloroethane; or tertiary amides such as dimethylformamide (DMF). Tertiary amides are particularly suitable, and DMF is most preferred. Other suitable reaction vehicles known to the skilled person may also be used. The ratio by weight of reaction vehicle to total carbohydrate during the chlorination reaction may be about 5:1 to about 12:1.

The chlorinating agent is preferably added in excess with respect to the sucrose-6-acylate, and preferably in large excess. At least three molar equivalents of chlorinating agent are required per mole of sucrose-6-acylate in order to chlorinate the 4, 1' and 6' positions; thus, an excess amount of chlorinating is any amount above three molar equivalents per mole. In a preferred embodiment, the chlorinating agent is added in an amount of at least seven molar equivalents per mole of the sucrose-6-acylate. Typically, the molar ratio of the chlorinating agent to the sucrose-6-acylate is about 7:1 to about 11:1.

A number of reaction conditions can be used to achieve the chlorination according to the present invention. Walkup, U.S. Pat. No. 4,980,463, the disclosure of which is incorporated herein by reference, for example, discloses a two stage process in which chlorination is carried out at two different temperatures, a temperature not higher than about 85° C. and a temperature of at least about 100° C. but not higher than about 130° C. to effect chlorination. Fry, U.S. 2007/0100139, the disclosure of which is incorporated herein by reference, discloses a process in which the reaction mixture is heated between 75° C. to 100° C. to effect chlorination.

In general, the reaction temperature for the chlorination reaction according to the present invention is typically from 85° C. to 130° C.

The reaction time for the chlorination according to the present invention depends on the temperature employed, with lower temperatures requiring longer reaction times. The skilled person can easily determine the optimum reaction time for a given reaction temperature by monitoring the reaction. If the reaction time is too short, insufficient conversion to the 4,1',6'-trichloro-4,1',6'-trideoxy-galactosucrose-6-acylate occurs. If the reaction time is too long, over-chlorination will occur, resulting in increased levels of tetra-chlorinated by-products.

Following chlorination, the process stream is quenched with an aqueous solution of a base to provide a sucralose-6-acylate and the chloride salt of the base. According to the present invention, the aqueous solution of a base must be of sufficiently high concentration that at least a portion of the chloride salt is formed as a precipitate; in other words, the concentration of the aqueous solution of the base must be sufficiently high that there is not enough water present in the process stream to maintain all of the chloride salt in solution.

A number of different bases may be used in the quenching. Preferred bases for quenching include alkali metal or alkaline earth metal hydroxides, or ammonium hydroxide. As alkali metal hydroxides, sodium and potassium hydroxide are particularly suitable. As an alkaline earth metal hydroxide, calcium hydroxide is particularly suitable. The most preferred base for quenching is sodium hydroxide, due to its ready availability and low cost. Other bases known to the skilled person may also be used for quenching.

An appropriate concentration of the aqueous solution of the base for quenching can be readily determined by the skilled person, by simple experimentation. If the concentration is too low, then the chloride salt of the base will remain in solution, and no precipitate will form. On the other hand, if the concentration of the base is too high, then it can be difficult to control the pH of the system, and there may be increased decomposition of the reaction vehicle. A concentration between these two extremes is most suitable in the context of the present invention.

Although an appropriate concentration of the aqueous solution of the base can be readily determined by experimentation, it may be noted that, when sodium hydroxide solution is used for quenching, precipitation is typically first observed at a concentration of above about 12% w/w. At concentrations up to around 35% w/w, good pH control remains possible. At higher concentrations, up to around 50% w/w, the advantages of the present invention are still evident, but it is more difficult to control the pH of the system. Thus, suitable concentrations include those in the range of 12 to 50% w/w, concentrations in the range of 25 to 45% w/w being preferred, and a concentration of around 35% w/w being most preferred.

Where bases other than sodium hydroxide are used for quenching, molar concentrations equivalent to the above concentrations are a good guide for selecting an appropriate concentration. Thus, concentrations in the range of 3.39 M (equivalent to 12% w/w NaOH solution at 20° C.) to 19.07 M (equivalent to 50% w/w NaOH solution at 20° C.) may be used, and a concentration of about 12.07 M (equivalent to 35% w/w NaOH solution at 20° C.) is preferred.

During the quenching, the pH of the process stream should preferably be controlled, since it is generally preferred that deacylation should be minimised while quenching takes place. This pH control is readily achievable by controlling the addition rate of the aqueous solution of the base while monitoring the pH within the process stream. Any method of pH-controlled addition known to the skilled person may be used.

Suitably, the pH of the stream is maintained in the range of from about 7.5 to about 10.5 during the quenching, more preferably from about 8.5 to about 9.75. Optionally, the pH may be maintained at a lower level, for example about 4.5, during the addition, and then raised to the preferred pH when all of the base has been added. A pH of more than about 10 should generally be avoided during quenching, though, since deacylation may then occur. In order to avoid local extremes of pH, the reaction mixture should be adequately mixed throughout the quenching procedure.

The temperature of the stream during quenching may suitably be maintained in the range of from above 0° C. to about 80° C., with a range of from about 12° C. to about 35° C. being preferred.

The quench may be conducted by the "dual stream quench" method, which is described in U.S. Pat. Nos. 5,530,106 and 5,498,709.

In the dual stream process, the quenching conditions are attained by slow addition of the aqueous base with simultaneous slow addition of feed material into a reaction vessel. The reaction vessel can contain an initial charge of an aqueous solution of the reaction vehicle, such as DMF. Slow addition of aqueous base and feed material allows both the pH and the temperature to be controlled during addition. The feed material and aqueous base are simultaneously added slowly until the desired quantity of feed material has been added. Further aqueous base is added until the desired pH is reached. Then the temperature and pH are maintained at the desired levels for the remainder of the reaction.

Quenching may alternatively be carried out by a circulated process. In the circulated process, the quenching conditions are attained by circulating feed mixture from a vessel through a circulation loop. Feed mixture and aqueous base are added slowly into this circulation loop. Slow addition of aqueous base and feed material allows both the pH and the temperature to be controlled during addition. Sufficient aqueous base is added until the desired pH is reached. Then the temperature and pH are maintained at the desired levels for the remainder of the reaction. This process may be run in a batch or continuous mode.

Following completion of the quenching, the process stream comprises a slurry of sucralose-6-acylate and precipitated salt in reaction vehicle and water, together with other minor components. This slurry may be deacylated directly, and the precipitated salt can then be removed from the stream after deacylation. Alternatively, the precipitated salt can be removed from the slurry before deacylation, and deacylation can be carried out on the desalinated process stream.

Regardless of the order in which the deacylation and salt removal are carried out, the deacylation is carried out with a base. Any suitable base may be used, and suitable bases are those already mentioned as the base for quenching. For convenience, it is preferred to use the same base for deacylation and quenching. It is particularly preferred to use sodium hydroxide as the base in both cases.

In order to effect deacylation, it is necessary to raise the pH of the stream, typically to a level above that at which the quenching was carried out. In order to minimise decomposition of the reaction vehicle, the deacylation is preferably carried out under carefully controlled conditions. Therefore, according to the present invention, the deacylation is preferably performed at a pH of from 10 to 13.5, more preferably from 10 to 12, and most preferably from 10.5 to 11.2, at a temperature of from 60 to 0° C., more preferably from 40 to 0° C., and most preferably from 35° C. to 25° C., the higher pH being used with the lower temperature and vice versa.

The deacylation reaction can be conveniently monitored by HPLC. For optimum yields, it is important to monitor the progress of the deacylation reaction, and neutralise the reaction mixture when the reaction is complete. The pH of the reaction mixture should be adjusted to from 6 to 8.5, preferably approximately 7.5. The reaction mixture can conveniently be neutralised using aqueous hydrochloric acid, or using citric acid or acetic acid. Alternatively, the reaction mixture can be neutralised with gaseous carbon dioxide.

The concentration of the base used for deacylation is preferably as given above for the base used for quenching. The use of such high concentrations ensures that salts are not re-dissolved in the case where the slurry is deacylated, and ensures that unnecessary amounts of water are not added to the process stream in the case where a desalinated stream is deacylated. As with the quenching procedure, adequate mixing should be employed to avoid local extremes of pH.

The quenching and deacylation can be carried out in a batch or continuous manner and may be carried out in a single vessel or in multiple vessels. Equally, a combination transitioning between continuous and batch from one or more vessels to one or more vessels can be used. The choice of arrangement will be dictated by practical considerations.

Although quenching and deacylation are carried out sequentially in the preferred embodiment described above, it is also possible for quenching and deacylation to be carried out together. In this embodiment, the aqueous solution of a base is added to the chlorination product stream exactly as described above for quenching, but with the exception that the pH of the stream is allowed to rise immediately to a level where deacylation can occur, rather than being controlled to minimise deacylation. Suitable pH conditions for effecting deacylation are discussed above, and are equally applicable here.

Prior to the removal of precipitated salt from the process stream, the stream may optionally be concentrated to at least partially remove water, and optionally also some reaction vehicle. This causes further salt to be precipitated, so that an even greater proportion of the salts can be removed from the process stream.

The removal of salts from the process stream, either from the slurry or from the deacylated stream, can take place by any suitable technique known to the skilled person. Preferably, the removal of the precipitated salts is carried out by filtration. Suitable filtration techniques include rotary vacuum filtration apparatus, a pressure filter apparatus, or a gravity filter apparatus, and such filtration apparatus can be advantageously incorporated in the quenching and/or deacylation vessel. Non-filtration techniques may also be used, and suitable non-filtration techniques include a centrifuge, a cyclone, or decantation.

The advantages associated with the present invention are observed when at least a portion of the salts are removed, and the advantages become more pronounced as more salt is removed. The amount of salt that is removed will depend mainly upon what proportion of the salt is formed as a precipitate during quenching.

Regardless of the point at which the salts are removed from the process stream, it is preferred that at least half of the total salts present in the mixture at that stage are removed. More preferably, at least two-thirds of the total salts are removed. In one preferred embodiment, at least 85% is removed.

Following their removal from the product stream, the precipitated salts are preferably washed with a suitable washing solvent to recover any sucralose or sucralose-6-acylate that may have been removed with the precipitate, and to thereby maximise the yield of the desired product. The washing liquor is then preferably returned to an appropriate process stream.

Suitable washing solvents can be solvents in which the sucralose/sucralose-6-acylate is soluble but the precipitated salts are not soluble. For example, the washing solvent may be the same as the reaction vehicle.

Alternatively, if the quantity used is carefully controlled, water can be used as the washing solvent without significant quantities of salts being re-dissolved. This has the advantage that the salts are obtained in a clean form, that is substantially free of reaction vehicle. The salts can then be used directly for another application, without the need for any further processing. Brine solutions, and more particularly saturated brine solutions, may also be used as the washing solvent. This further reduces the quantity of salts that is re-dissolved, while still resulting in recovered salts that are substantially free of reaction vehicle and can be used directly for another application.

Following the deacylation reaction and removal of the precipitated salts, the sucralose may be isolated from the resulting sucralose product stream. Preferably, the reaction vehicle remaining in this product stream is at least partially removed from the product stream, and isolation of sucralose then takes place from the resulting product stream.

The removal of reaction vehicle can be carried out by means known in the art, such as distillation, distillation under reduced pressure, steam distillation, steam stripping, or by use of an agitated thin film drier or spray drier. When the reaction vehicle is a tertiary amide, it is preferred that the removal of the reaction vehicle is carried out by steam stripping. Such steam stripping can be carried out as described in EP 0708110. Typically, at least 90% of the reaction vehicle present in the mixture at the end of deacylation is removed during this step. More typically, at least 99% is removed.

When carried out in the context of the present invention, steam stripping to remove reaction vehicle requires substantially less energy than in prior art processes, since far less water is present in the product stream. Energy costs for the steam stripping can thus be reduced by as much as 75-80%. The environmental impact of the process is thus significantly reduced.

In addition to the advantages already mentioned, the removal of salts from the sucralose product stream also opens up the possibility of employing salt-sensitive processing steps on the downstream product stream. The presence of high concentrations of salts in prior art sucralose product streams prevented such processing steps from being able to be used.

The present inventors have recognised a particularly beneficial opportunity to take advantage of the low salt product stream provided according to the present invention. In particular, they have recognised that the low salt product stream can be subjected to an improved process for the removal of dimethylamine (DMA).

DMA is the hydrolysis product of DMF. When DMF is used as reaction vehicle in the chlorination of sucrose-6-acylate and in the subsequent deacylation of sucralose-6-acylate, the reaction conditions, and in particular the elevated pH during the deacylation step, result in some DMF hydrolysis and consequent formation of DMA. Typically, around 4-20 moles of DMF are converted to DMA per mole of sucralose.

DMF hydrolysis to produce DMA is undesired for a number of reasons. A first reason is that the DMF that is converted to DMA cannot be directly recycled for re-use in the sucralose production process. This loss of valuable DMF imposes a significant financial burden on the process. A further reason is that the presence of DMA in product and waste streams causes difficulties in downstream processing steps.

One possible strategy for removing DMA from a sucralose product stream is to increase the pH in order to free the DMA from its counter-ion containing salts, and to then remove the relatively volatile free DMA by applying heat and reduced pressure. However, these conditions can result in degradation of sucralose and other valuable carbohydrates in the stream, and are also expensive to apply. Accordingly, it would be advantageous to be able to remove DMA under more gentle conditions, so as to maintain the yield of sucralose and other valuable carbohydrates.

It has now been found that DMA can be effectively removed from a low salt product stream, such as that provided according to the present invention, by making use of a cation exchange resin. This technique cannot be used on sucralose product streams according to the prior art, since the high concentration of salts in such streams renders the cation exchange resin ineffective. This is because the cations from the salts present in the streams (such as $Na^+$ ions from NaCl) occupy the binding sites of the cation exchange resin, so that few or no binding sites are available to bind DMA (in the form of its cation, $DMAH^+$, which has a $pK_a$ of 10.73). In the case of low salt product streams, however, this problem is significantly reduced, so that effective binding of $DMAH^+$ to the cation exchange resin is possible.

Thus, according to a further aspect of the present invention, there is provided a process according to the first aspect of the present invention, wherein the process further comprises contacting the product stream of (iii), i.e. an at least partially desalinated sucralose product stream, with an ion exchange resin.

Preferably, the contacting of the product stream with the ion exchange resin takes place by passing the stream through a column loaded with the ion exchange resin or through a bed comprising the ion exchange resin.

Suitable cation exchange resins for use with the present invention are those that can bind $DMAH^+$ while allowing sucralose and other valuable carbohydrates to pass through substantially unchanged. Strong acid cation exchange resins, such as those containing a sulfonate group or other acidic group, have shown themselves to be particularly suitable, and are preferred. Particularly preferred examples of suitable cation exchange resins are Purolite® C120E (available from Purolite) and Dowex® HCRS (available from Dow). Other cation exchange resins that would be suitable for use in the present invention include Purolite® C100E (available from Purolite), Finex® CS 08 G (available from Finex), Finex® CS 12 G (available from Finex), Finex® 18 G (available from Finex), Purolite® C100 series (available from Purolite), Purolite® C150 series (available from Purolite), Purolite® PCR series (available from Purolite), Amberlite® IR120 series (available from Rohm & Haas), and DIAION® SK, PK, and UBK series (all available from Mitsubishi Chemical). Yet further cation exchange resins that may be contemplated for use in the present invention include Dowex® 88 (available from Dow) and Purolite® 104E (available from Purolite).

According to a preferred embodiment, the removal of DMA from a sucralose product stream of the present invention takes place after reaction vehicle (DMF) has been at least partially removed from the desalinated product stream, which will preferably have taken place by steam stripping. The product stream will therefore be essentially aqueous. If necessary, further water can be added to dilute the product stream and to adjust the viscosity as required.

In order to protect the cation exchange resin, it is preferable to subject the product stream to a filtration step prior to contacting it with the cation exchange resin. Any suitable filtration procedure known to the skilled person can be used for this purpose.

The cation exchange resins for use in the present invention can be prepared according to techniques known in the art. A preferable method for preparing the cation exchange resins for use is to treat them either with a sodium chloride solution or with a sodium hydroxide solution. These solutions are known as "regenerants". In the case of a sodium chloride solution, the preferred solution concentration is from 5 to 20%, and is most preferably about 10%. In the case of a sodium hydroxide solution, the preferred solution concentration is from 2 to 20%, and is most preferably around 5%. Following the treatment with regenerant, the resins are rinsed with deionised water. In the case where a sodium chloride solution is used as regenerant, rinsing is preferably continued until the sodium chloride content of the rinse water reaches about 400 ppm or lower. In the case where a sodium hydroxide solution is used as regenerant, rinsing is preferably continued until the pH of the rinse water reaches about pH 10 or lower.

Following preparation of the cation exchange resin, for example as set out above, it can be packed to form a resin bed/loaded to form a resin column. The quantity of resin used for a particular volume of feed stream can be selected by performing preliminary calculations and optimisation experiments for the particular resin and feed stream used.

The total ion exchange capacity of an ion exchange resin is the theoretical maximum quantity of ions that can be bound by a particular resin, and will generally be advertised by the manufacturer. In general, this parameter is quoted in units of "equivalents per liter of resin". If a particular resin has a total ion exchange capacity of 1 equivalent per liter, then it is theoretically capable of binding a maximum of one mole of singly-charged ions per liter of resin.

While the total ion exchange capacity of a particular ion exchange resin will generally be known, it should be noted that the operating capacity of the resin in a particular system will often be less than the total ion exchange capacity. The operating capacity can be calculated by routine experimentation for any particular system.

In addition to the operating capacity of the resin being used, additional parameters that can usefully be calculated are the number of equivalents of the ion to be removed per liter of feed stream (in the present case, this will be the number of moles of DMAH$^+$ per liter of feed stream) and the volume of feed stream to be treated.

With the above parameters to hand, it is possible to calculate the amount of feed (in liters) that can be treated by a given volume of resin as follows:

$$\frac{\text{Volume of Resin (L)} \times \text{Operating Capacity of Resin (Equivalents per Liter)}}{[\text{Equivalents of DMAH}^+ \text{ (moles per Liter of feed)}/\text{Volume of Feed (L)}]}$$

The above information, together with routine experimentation, will allow the skilled person to optimise the system for particular resins and feed concentrations.

Following preparation of the resin bed/column, the product stream can then be passed through the resin to at least partially remove DMA. The more salts that can be removed from the sucralose product stream prior to its being contacted with a cation exchange resin, the more effective the binding of DMAH$^+$ to the resin will be, and the more DMA will therefore be removed. Accordingly, in this aspect of the present invention, it is preferred to remove as much salt as practicable from the product stream prior to its being contacted with a cation exchange resin, while keeping cost and the overall efficiency of the process in mind. Thus, it is preferred to remove at least 50% of the salts, more preferably at least 75% of the salts, and most preferably at least 85% of the salts prior to the contacting of the product stream with the cation exchange resin. Furthermore, when practising this further aspect of the present invention, it is generally preferred to include the optional procedure of concentrating the stream prior to the removal of precipitated salt, to at least partially remove water, and optionally also reaction vehicle, from the stream, and to thereby cause further salt to be precipitated. This optional procedure is discussed in detail above in connection with the first aspect of the present invention.

As has been discussed previously, it is desirable to wash the precipitated salts following their removal from the product stream, in order to recover any sucralose or other valuable carbohydrates that may have been removed with the precipitated salts. The washing liquor can then be added back into the product stream in order to maintain yields. In the case where it is intended to contact the product stream with an ion exchange resin, it may often be preferable to combine the washing liquor from the washing of the precipitated salts with the product stream downstream of the product stream being contacted with the ion exchange resin. The reason for this is that, while this washing liquor may contain valuable carbohydrates, it may also include some re-dissolved salts.

The conditions for achieving optimum performance of the cation exchange resins used in the present invention may vary according to the resin used and can be determined by routine experimentation. As a guide, optimum performance of the cation exchange resins might be expected when the pH of the product stream is in the range of from about 7 to about 9, and preferably around 7, and when the temperature of the product stream is in the range of from about 10 to about 50° C., and preferably around room temperature.

The amount of DMA that can be removed from the product stream according to this aspect of the present invention will vary according to the factors already mentioned, such as the concentration of residual salts, temperature and pH of the product stream and so on. However, in general, it is preferred that at least 70% of the DMA present prior to contacting the stream with cation exchange resin is removed, more preferably at least 95%, and most preferably at least 99%.

After use, i.e. after the resin's capacity to bind further DMAH$^+$ is no longer sufficient, the resin bed/column is preferably flushed with deionised water to remove any sucralose and other valuable carbohydrates, and the flush liquor can then be combined with the remaining product stream to maintain yields.

Removal of bound DMAH$^+$ from the cation exchange resin is preferably carried out in the same manner as the initial preparation of the resin detailed above, i.e. by treating with a regenerant and then rinsing with deionised water. Following this, the resin is ready to be reused.

In a particularly preferred embodiment, the recovered DMA is subjected to conditions effective to convert it back into DMF. An example of appropriate conditions for effecting this conversion is the use of carbon monoxide and catalytic amounts of sodium methoxide. This conversion is known in the art, and so no further details need be given here. The regenerated DMF can then be reused as the reaction vehicle in the production of sucralose. This recovery of DMF that would have been lost in prior art processes provides a significant economic as well as an environmental advantage.

Eventual isolation of sucralose in the method of the present invention will usually be carried out as described in EP 0708110.

The second aspect of the present invention provides a method for producing a sucralose-6-acylate product stream from a feed stream comprising a sucrose-6-acylate in a reaction vehicle. The sucralose-6-acylate product stream may be further processed to form final products such as sucralose, or the sucralose-6-acylate may simply be isolated as the final product.

It will be clear that the process according to the second aspect of the invention is analogous to the process according to the first aspect of the present invention, differing mainly in that the deacylation of the sucralose-6-acylate to form sucralose need not take place. Thus, the process according to the first aspect of the invention is carried out until the quenching is complete, and precipitated salt is removed from the slurry to form the desired sucralose-6-acylate product stream.

It will be noted that all preferred features of the second aspect of the invention have already been described with reference to the first aspect of the present invention. Thus, reference should be made to the description given in respect of the first aspect, which applies equally to the second aspect.

If sucralose-6-acylate is the desired end product of the process according to the second aspect of the invention, then it may be isolated by any of the methods known to those skilled in the art. An appropriate method for its isolation is known from U.S. Pat. No. 4,980,463, for example.

The sucralose-6-acylate product stream produced according to the second aspect of the present invention may also be subjected to further processing. For example, the sucralose-6-acylate may be converted to sucralose, and sucralose can then be isolated from the resulting product stream. The conversion of sucralose-6-acylate to sucralose may be carried out by any means known to those skilled in the art. An example of appropriate conditions for effecting the conversion is given above with reference to the first aspect of the present invention.

The invention will now be illustrated by means of the following examples, it being understood that these are intended to explain the invention, and in no way to limit its scope.

EXAMPLES

In what follows, all % amounts are by weight (w/w), unless otherwise stated.

General:

The feed stream came from the acetylation of sucrose. Such a feed stream can be produced, for example, by the methods disclosed in U.S. Pat. No. 5,470,969. A typical composition of the feed stream is as follows:

| Description | % of total, w/w |
|---|---|
| Sucrose-6-acetate | 29.4 |
| Other carbohydrates | 10.4 |
| DMF | 52.7 |
| Others | 7.5 |

Chlorination:
1. A hot oil bath was preheated to 105° C.
2. 50 grams of the acetylated feed material was charged to a 500 ml flask equipped with a stirrer bar.
3. Approximately 75 grams of reagent DMF was charged to the flask.
4. The flask was cooled to 5-10° C. in an ice bath.
5. 50 grams of Arnold's reagent (chloromethylene dimethyl ammonium chloride) were slowly added to the flask while maintaining a temperature of less than 30° C. The addition was carried out under an atmosphere of nitrogen. The mixture was then stirred for 30 minutes.
6. The flask was placed in the prepared hot oil bath and a condenser and centre stopper were fitted.
7. The mixture was held with stirring for 5-6 hours. The bath and flask temperature were measured about every 30 minutes.
8. The flask was removed from the hot oil bath and rapidly cooled to 15° C., using an ice bath.

Quenching

Example 1

500 g of chlorination mass was pumped at the rate of 2.8 g/min into a temperature controlled vessel with pH control using a pump feeding 35% NaOH. Initially, the pH set point was set to 8.5 until all of the feed had been added slowly with the pot temperature controlled to 19° C. After all of the feed had been added and 138 g of 35% NaOH used, the pH set point was raised to 9.5 or retained at 8.5 and additional NaOH solution was added as necessary. Raising the pH set point of titration to 9.5 consumed an additional 6 g of 35% NaOH. This resulted in a solution containing a concentration of sucralose-6-acetate of 5.1% and a concentration of sucralose of 0.15%. The solvent, DMF, had a concentration of 60.1% w/w. A wet salt cake of 111.2 g was produced, from which it was possible to extract 1.6 g of sucralose-6-acetate and 0.6 g of sucralose. Dimethyl amine (DMA) recovered totalled 19.4 g with this approach.

Example 2

Comparative

A control run was performed using 11% NaOH in order to avoid salt precipitation and to provide comparative concentrations to demonstrate the improvement possible with using the higher concentrations. 500 g of chlorination mass was pumped at the rate of 5.6 g/min into a temperature controlled vessel at 19° C. 11% NaOH was added to a pH set point of 9.5, consuming 454 g of 11% NaOH. This resulted in a final concentration of 2.8% of sucralose-6-acetate and 0.2% of sucralose. The solvent (DMF) concentration was only 36.2% w/w. 19.9 g dimethyl amine was recovered. However, the much more dilute solution increases substantially the energy cost of DMF removal.

Example 3

Another run was performed using 500 g of chlorination mass and 35% NaOH to neutralize the reaction mass. However, the initial pH for neutralization was set to pH 4.5 until all of the feed had been added (1.7 g/min). The pH was slowly raised to 8.5 with 35% NaOH. The concentration of sucralose-6-acetate was 4.9% and the concentration of sucralose was 0.1%. The solvent (DMF) concentration was 58.3% w/w. 25.0 g of DMA was recovered.

Example 4

A run was performed using 500 g of chlorination mass and 30% NaOH to neutralize the reaction mass. The initial pH was maintained at pH 4.5 until all feed had been added. The pH was then raised to pH 8.5 with 30% NaOH. The concentration of sucralose-6-acetate was 4.8% and the concentration of sucralose was 0.1%. Solvent (DMF) concentration was 55.1% w/w and 28.2 g of DMA was produced.

Example 5

500 g of chlorination mass was neutralized with 50% NaOH. The reaction had a tendency when neutralized to pH 4.5 to then slowly rise in pH. It was observed that quenching to pH 4.5 and then raising pH gave similar carbohydrate yields but increased dimethyl amine concentrations. The sucralose-6-acetate concentration reached 5.016% with sucralose at 0.23%. The solvent (DMF) concentration reached 61.6% (w/w).

Example 6

500 g of chlorination mass was neutralized with 40% NaOH. Tendencies similar to the quench with 50% NaOH were noted, with a tendency for the pH to continue rising following cessation of addition of NaOH. Allowance for this tendency enables operation at these conditions. Sucralose-6-acetate concentration reached 4.93% with sucralose at 0.181% and DMF at 60.6% w/w.

A summary of the resultant product streams for the above examples is given below:

| | g | | DMF |
|---|---|---|---|
| NaOH Concentration | Total (sucralose + sucralose-6-acetate) | Dimethylamine (DMA) | Concentration % w/w |
| 35% (Eg. 1) | 29.9 | 19.4 | 60.1 |
| 11% (Comp. Eg. 2) | 28.9 | 19.9 | 36.2 |
| 35% (Eg. 3) | 29.0 | 25.0 | 58.3 |
| 30% (Eg. 4) | 29.4 | 28.2 | 55.1 |
| 50% (Eg. 5) | 28.0 | 29.9 | 61.6 |
| 40% (Eg. 6) | 28.4 | 30.0 | 60.6 |

Quenching Followed by Filtration

Example 7

2371 g of chlorination mass was quenched to a target of pH 8.5 with 35% NaOH. A wet salt cake was separated by filtration and the filtrate was found to contain 5% sucralose-6-acetate plus sucralose, and 58.05% w/w DMF.

Deacylation of a Filtrate

Example 8

463 grams of the filtrate from Example 7 was deacetylated at pH 11.45 and 30° C. with 50% NaOH, producing a solution containing 4.6% sucralose plus sucralose-6-acetate, with DMF at 54.28%, and an additional 76 g of a wet salt cake.

Example 9

Comparative

The stream obtained in Example 2 (Comparative) was deacetylated using 23% NaOH at pH 11.2, 30° C. to produce a solution containing 2.59% sucralose and sucralose-6-acetate with only 33% DMF. No salt cake was produced.

Deacylation of a Slurry

Example 10

500 g of chlorination mass was quenched at pH 9.6 with 35% NaOH and then deacetylated at pH 11.7, 22° C. with 50% NaOH. The resultant 745 g neutralized slurry was filtered producing a 628 g filtrate and a wet salt cake of 109 g. The filtrate contained 50% DMF and 5.25% sucralose and sucralose-6-acetate.

Example 11

Comparative 500 g of chlorination mass was quenched with 11% NaOH producing a solution containing 32% DMF and 3.0% sucralose and sucralose-6-acetate. The solution was deacetylated with 23% NaOH at pH 11.7, 22° C. to produce a 1123 g solution containing 29% DMF and 2.5% sucralose and sucralose-6-acetate. No salt cake was produced.

Combined Quenching and Deacylation

Example 12

500 g chlorination mass received 50% NaOH slowly via dual simultaneous addition of carbohydrate stream and caustic. The pH was allowed to rise past the neutralization target of 8.5 following addition of all of the carbohydrate stream. The temperature was controlled at 12° C. with pH 12.4 to effect deacylation of the carbohydrate. The DMF concentration following 4 hours under the above conditions after lowering the pH to 8.5 with HCl reached 61% (w/w). Remaining sucralose-6-acetate plus sucralose reached 4.1% w/w without additional concentration.

Example 13

500 g of chlorination mass received 50% NaOH slowly via dual simultaneous addition of carbohydrate stream and caustic. The pH was allowed to rise past the neutralization target of pH 8.5 following addition of all of the carbohydrate stream. However, for deacetylation, a higher temperature (40° C.) with a lower pH (10.7) was used. DMF concentration reached 64% w/w with sucralose and sucralose-6-acetate reaching above 5%.

Example 14

500 g of chlorination mass was quenched at pH 11.7, 22° C. with 35% NaOH and then held at pH 11.7, 22° C. with 50% NaOH to continue deacetylation. This expedited processing by combination of quench and deacetylation. A neutralized slurry of 754 g was produced which was filtered to obtain a 634 g filtrate and a 113 g wet filter cake. The filtrate contained 4.65% sucralose and sucralose-6-acylate and 52% DMF.

Deacylation with Subsequent Concentration

Example 15

500 g of chlorination mass was quenched to pH 9.5 using 35% NaOH and then deacetylated at pH 11.7, 22° C. to produce a neutralized slurry with insoluble salt. The 739 g slurry was concentrated under vacuum to produce a 425 g slurry which was separated via filtration to a 285 g filtrate and a 128 g wet salt cake. The filtrate contained 10.45% sucralose and sucralose-6-acetate and 59% DMF.

Removal of DMA Using Ion Exchange Resins

Example 16

In order to demonstrate the removal of DMA from a low salt sucralose product stream using cation exchange resins, the following procedures were carried out:

Preparation of the Resin Bed:

A resin bed was prepared by washing a strong cation exchange resin, such as Dowex® HCRS or Purolite® C120E, with either 10% NaCl or 5% NaOH. The washed resin was then packed with deionised water to form a resin bed, and then flushed with deionised water to flush the resin bed of regenerate.

Preparation of a Suitable Test Stream:

A test stream was prepared by following the procedures described in EP0708110 to obtain deacetylated steam strip bottoms.

Removal of Salts:

Salts were removed from the test stream by evaporating water to cause precipitation of the salts and subsequent filtration to remove the precipitated salts. If necessary, the filtrates were diluted with water to adjust the viscosity. The filtrates were then used in the Examples below:

Example 16a

Comparative

A filtrate containing 5.4 wt % sucralose, 8 wt % chloride, 35,000 ppm sodium ions and 23,000 ppm DMA was charged to the prepared resin bed (Dowex® HCRS) such the total amount of DMA applied was 35.8 g. The bed was then rinsed with deionised water and the effluent was analysed for its DMA content. It was found that 4 g of DMA had bound to the resin. A resin capacity of 0.32 equivalents per liter of resin was thereby calculated.

Example 16b

A filtrate stream containing 15 wt % DMA and 2.3 wt % sodium was diluted with water to adjust its viscosity. This stream was charged to a bed of Dowex® HCRS resin prepared as above, in an amount of 3 equivalents of DMA per liter of packed resin. The bed was then rinsed with deionised water and the effluent was analysed for its DMA content. It was found that 78% of charged DMA had bound to the resin.

Example 16c

The Example 16b was repeated but 2 equivalents of DMA per liter of packed resin was charged to the resin bed. It was found that 92% of charged DMA was retained on the resin.

Example 16d

The Example 16b was repeated but 1 equivalent of DMA per liter of packed resin was charged to the resin bed. It was found that 100% of charged DMA was retained on the resin.

Example 17

In order to further demonstrate the removal of DMA from a low salt sucralose product stream using cation exchange resins, the following procedures were carried out:

Sucralose-6-acetate was subjected to chlorination according to the procedures described in EP0708110 to provide a chlorination mass.

1646 g of the chlorination mass (36.5% DMF, 2.4% sucralose-6-acetate, 29000 ppm DMA, 7.4% chloride) was deacetylated for 6 hours at pH 12.4, 11.4° C. by addition of 10% NaOH. Concentrated HCl was used to reduce the pH to 8.3. 2090 g product was collected containing 2.2% sucralose, 6.9% (142 g) chloride, and 15600 ppm DMA (32 g DMA total). 2067 g of this material was concentrated to 686 g which was filtered producing a 229 g wet salt cake and 461 g concentrated filtrate. The concentrated filtrate contained 60700 ppm DMA (28 g) and 56% DMF (258 g).

The concentrated filtrate obtained above was diluted 1:4 with water to adjust its viscosity and was then run through a column packed with 1.3 L Mitsubishi UBK 510L resin (prepared by washing with 5% NaOH and rinsing with deionised water). The column was washed with deionised water to displace carbohydrate and 2227.3 g effluent was collected. This contained 11.5% (257 g) DMF, 0.2% chloride (4.5 g) and 321 ppm DMA (0.72 g). The DMA removal in this case was 97.4%.

The invention claimed is:

1. A method for producing sucralose from a feed stream comprising a sucrose-6-acylate in a reaction vehicle, wherein said method comprises:
   (i) reacting the sucrose-6-acylate with a chlorinating agent in order to chlorinate the 4, 1' and 6' positions of the sucrose-6-acylate;
   (ii) quenching the product stream of (i) with an aqueous solution of a base to provide a sucralose-6-acylate and the chloride salt of said base, wherein the concentration of the aqueous solution of the base is sufficiently high such that at least a portion of the chloride salt of the base is formed as a precipitate; and
   (iii) either:
      deacylating the sucralose-6-acylate by treating the product stream of (ii) with a base and thereafter removing precipitated salt to provide a product stream comprising sucralose;
   or:
      removing precipitated salt from the product stream of (ii) and thereafter deacylating the sucralose-6-acylate by treating with a base to provide a product stream comprising sucralose.

2. A method according to claim 1, further comprising:
   (iv) isolating sucralose from the product stream of (iii).

3. A method according to claim 1, wherein the base used for quenching in (ii) is an alkali metal or alkaline earth metal hydroxide, or ammonium hydroxide.

4. A method according to claim 3, wherein the base used for quenching in (ii) is sodium hydroxide.

5. A method according to claim 4, wherein the sodium hydroxide is provided as an aqueous solution having a concentration of from 12% w/w to 50% w/w.

6. A method according to claim 1, wherein the pH of the stream is maintained in the range of from 7.5 to 10.5 during the quenching (ii).

7. A method according to claim 1, wherein the temperature of the stream is maintained in the range of from above 12° C. to 35° C. during the quenching (ii).

8. A method according to claim 1, wherein the pH of the stream is allowed to rise to between 10 and 12 during the quenching (ii), such that deacylation of the sucralose-6-acylate also takes place to at least some extent.

9. A method according to claim 8, wherein the temperature of the stream is maintained in the range of from 0 to 40° C. during the quenching (ii).

10. A method according to claim 1, wherein prior to the removal of precipitated salt, the stream is concentrated to at least partially remove water, and optionally also reaction vehicle, in order to cause further salt to be precipitated.

11. A method according to claim 1, wherein the precipitated salt is removed by filtration.

12. A method according to claim 1, wherein the precipitated salt is removed by a non-filtration technique.

13. A method according to claim 1, wherein the precipitated salt is washed with a washing solvent, and the resulting washing liquor is returned to the stream.

14. A method according to claim 13, wherein the washing solvent is the same as the reaction vehicle, or is selected from water, a brine solution, or a saturated brine solution.

15. A method according to claim 1, wherein the sucralose-6-acylate is sucralose-6-benzoate or sucralose-6-acetate.

16. A method according to claim 1, wherein reaction vehicle is at least partially removed from the product stream of (iii), and isolation of sucralose takes place from the resulting product stream.

17. A method according to claim 16, wherein the removal of reaction vehicle is performed by steam stripping, or by use of an agitated thin film drier or spray drier.

18. A method according to claim 1, wherein the base used for deacylating the sucralose-6-acylate in (iii) is a metal or ammonium hydroxide.

19. A method according to claim 1, wherein deacylating the sucralose-6-acylate in (iii) is carried out at a pH of from 8 to 14 and a temperature of from 0 to 60° C.

20. A method according to claim 19, wherein deacylating the sucralose-6-acylate in (iii) is carried out at a pH of from 10 to 12 and a temperature of from 0 to 40° C.

21. A method according to claim 1, wherein the reaction vehicle comprises a tertiary amide.

22. A method according to claim 21, wherein the tertiary amide is dimethyl formamide (DMF).

23. A method according to claim 1, wherein the method further comprises contacting the product stream of (iii) with an ion exchange resin.

24. A method according to claim 23, wherein the ion exchange resin is a cation exchange resin.

25. A method according to claim 24, wherein a strong cation exchange resin is used as the cation exchange resin.

26. A method according to claim 23, wherein the contacting of the product stream with the ion exchange resin takes place after reaction vehicle has at least partially been removed from the product stream.

27. A method according to claim 23, wherein the product stream is essentially aqueous when contacted with the ion exchange resin.

28. A method according to claim 23, wherein the product stream is filtered prior to being contacted with the ion exchange resin.

29. A method according to claim 23, wherein the ion exchange resin is flushed with a flushing solvent after it has been contacted with the product stream, and wherein the flushing liquor thereby obtained is combined with the downstream product stream.

30. A method according to claim 29, wherein the flushing solvent is deionised water.

31. A method according to claim 23, wherein the ion exchange resin is treated with a regenerant after it has been contacted with the product stream.

32. A method according to claim 31, wherein the regenerant is selected from the group consisting of an aqueous sodium chloride solution or an aqueous sodium hydroxide solution.

33. A method according to claim 31, wherein the regenerant is subsequently collected.

34. A method according to claim 33, wherein the collected regenerant comprises dimethyl amine (DMA).

35. A method according to claim 34, wherein the DMA is subjected to reaction conditions effective to convert DMA into DMF.

36. A method according to claim 31, wherein the ion exchange resin is re-used after having been treated with the regenerant.

37. A method according to claim 23, wherein the precipitated salts are washed with a washing solvent, and the resulting washing liquor is combined with the product stream downstream of its being contacted with an ion exchange resin.

38. A method for producing a sucralose-6-acylate product stream from a feed stream comprising a sucrose-6-acylate in a reaction vehicle, wherein said method comprises:
(i) reacting the sucrose-6-acylate with a chlorinating agent in order to chlorinate the 4, 1' and 6' positions of the sucrose-6-acylate;
(ii) quenching the product stream of (i) with an aqueous solution of a base to provide the sucralose-6-acylate and the chloride salt of said base, wherein the concentration of the aqueous solution of the base is sufficiently high such that at least a portion of the chloride salt of the base is formed as a precipitate; and
(iii) removing precipitated salt from the product stream of (ii) to provide a sucralose-6-acylate product stream.

39. A method according to claim 38, further comprising isolating the sucralose-6-acylate from the product stream of (iii).

40. A method according to claim 38, further comprising the conversion of sucralose-6-acylate to sucralose to provide a sucralose product stream.

41. A method according to claim 40, further comprising isolating sucralose from the sucralose product stream.

* * * * *